United States Patent
Kaplan et al.

(10) Patent No.: US 11,458,324 B1
(45) Date of Patent: Oct. 4, 2022

(54) COSMETIC TREATMENT FOR REDUCING BODY SIZE

(71) Applicants: Andres Kaplan, Ramat Gan (IL); Florencia Kaplan, Ramat Gan (IL); Flavia Krsticevic, Ramat Gan (IL)

(72) Inventors: Andres Kaplan, Ramat Gan (IL); Florencia Kaplan, Ramat Gan (IL); Flavia Krsticevic, Ramat Gan (IL)

( * ) Notice: Subject to any disclaimer, the term of this patent is extended or adjusted under 35 U.S.C. 154(b) by 0 days.

(21) Appl. No.: 17/450,687

(22) Filed: Oct. 12, 2021

(51) Int. Cl.

| | |
|---|---|
| *A61N 1/44* | (2006.01) |
| *A61K 8/96* | (2006.01) |
| *A61Q 19/00* | (2006.01) |
| *A61K 8/92* | (2006.01) |
| *A61K 9/00* | (2006.01) |
| *A61B 18/00* | (2006.01) |
| *A61N 5/067* | (2006.01) |
| *A61N 5/06* | (2006.01) |
| *A61K 8/20* | (2006.01) |
| *A61K 8/35* | (2006.01) |
| *A61H 33/04* | (2006.01) |

(52) U.S. Cl.
CPC ............... *A61N 1/44* (2013.01); *A61H 33/04* (2013.01); *A61K 8/20* (2013.01); *A61K 8/35* (2013.01); *A61K 8/922* (2013.01); *A61K 8/965* (2013.01); *A61K 9/0009* (2013.01); *A61N 5/067* (2021.08); *A61N 5/0616* (2013.01); *A61Q 19/00* (2013.01); *A61B 2018/00464* (2013.01); *A61H 2033/046* (2013.01); *A61N 2005/0645* (2013.01); *A61N 2005/0652* (2013.01); *A61N 2005/0659* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 2014/0188071 A1* | 7/2014 | Jacofsky | A61N 1/327 604/501 |
| 2015/0094647 A1 | 4/2015 | Kalghatgi et al. | |
| 2017/0246440 A1 | 8/2017 | Kalghatgi et al. | |

OTHER PUBLICATIONS

YoungYou Pure Dead Sea Bath Salts, Detox & Slim, available at https://www.youngyouorganix.com/product/dead-sea-bath-salt-detox-and-cellulite-remover/ (2017).*
Moreira, J.S., et al., Plaster body wrap: effects on abdominal fat, Integr Med Res 2 (2013)151-156.*
Gelker, M., Müller-Goymann C., y W. Viöl. 2018. «Permeabilization of human stratum corneum and full-thickness skin samples by a direct dielectric barrier discharge.» Clinical Plasma Medicine 34-40.
Graves, D., Hamaguchi S., y D. O'Connell. 2015. «In Focus: Plasma Medicine.» Biointerphases.
Nikolis, A., MD, MSc, FRCSC, Kaitlyn M Enright, MSc, A Multicenter Evaluation of Paradoxical Adipose Hyperplasia Following Cryollpolysis for Fat Reduction and Body Contouring: A Review of 8658 Cycles in 2114 Patients, Aesthetic Surgery Journal, vol. 41, Issue 8, Aug. 2021, pp. 932-941, https://doi.org/10.1093/asj/sjaa310.
Sharma, Tanvi & Kanwar, Shamsher. (2018). Phytomolecules for Obesity and Body Weight Management. Biochemistry and Cell Biology. 1.
Zhai, M., Dazhi Yang, Weihong Yi & Wuping Sun (2020) Involvement of calcium channels in the regulation of adipogenesis, Adipocyte, 9:1, 132-141, DOI: 10.1080/21623945.2020.1738792.

* cited by examiner

*Primary Examiner* — H. Sarah Park
(74) *Attorney, Agent, or Firm* — Haim M. Factor—1st-Tech-Ideas.com

(57) ABSTRACT

A cosmetic treatment for reducing body size, incorporating a cosmetic minimally-invasive procedure (CMIP) and incorporating cold atmospheric plasma irradiation (CAP) of a body, the treatment comprising the five steps of: a first step of preparing a cosmetic composition and applying the composition to the body to form a mask on the body; a second step of using a gypsum plaster of Paris (POP) and sealing the mask; a third step of wrapping the POP with a nylon/plastic wrap; a fourth step of preparing the body with a layer of aqueous surface gel; and a fifth step of using CAP irradiation of the body; whereby the body is an abdominal region, and the body size is indicated by at least three representative body circumference measurements; and whereby body size reduction is statistically significant when comparing before and after cosmetic treatment body sizes.

12 Claims, 9 Drawing Sheets

COSMETIC TREATMENT FOR REDUCING BODY SIZE

FIELD OF THE INVENTION AND BACKGROUND

Embodiments of the current invention relate to cosmetic treatments and specifically to a cosmetic treatment for reducing body size. In the specification and claims hereinbelow, the expression "body size" is intended to mean and to be indicated by at least 3 representative body circumference measurements, as explained further hereinbelow.

Non-patent references are noted hereinbelow in the specification in most cases, by first author name. Complete reference information, listed alphabetically by first author name, is found in an IDS filed concurrently with the instant patent application.

The sense of beauty is changing throughout time with the improvement of cosmetic minimally-invasive procedures (CMIP) and the advance of ancillary new technologies. Nowadays, beauty is highly related to a healthy attitude (nutrition and exercise), with a preference to choose CMIP instead of submitting to risky cosmetic surgical procedures (CSP). According to the American Society of Plastic Surgeons (ASPS), CMIP increased 174% in the 10-year period from 2000-2020. In comparison, CSP dropped by 22% during the same period—all as reported by ASPS in 2020.

Body sculpting procedures in non-invasive fat reduction in the last decade has become one of the most requested procedures and is considered a new trend. Among the most important advantages of CMIP compared to the CSP are immediate results, affordable prices, and virtually no risk during CMIP.

Many innovations in CMIP have been developed, including: cryolipolysis (CoolSculpting®); high-intensity ultrasound energy (HIFU, Liposonix); electro-magnetic energy waves to induce rapid muscle contraction (EMEW, Emsculpt™); selective radiofrequency (RF, Vanquish™); low-level laser therapy (LLLT, Zerona™); whole body vibration (WBV); and extracorporeal shockwave therapy (ESWT)—all as known in the art.

Leading CMIP Techniques

The efficacy of CMIP techniques (such as, but not limited to: cryolipolysis; HIFU; RF; and LLLT) on body/waist circumference reduction as a sign of fat reduction are statistically significant, as described by Alizadeh et al. However, the effects on body contouring have been moderate (2-4 cm) after several treatment sessions or have had little or no effect. It is noteworthy to mention that virtually all CMIP techniques have no reports of clinical efficacy measures. The following is a brief description of some prior art techniques.

Cryolipolysis is the controlled application of cold to subcutaneous tissue to reduce adipose tissue. The treatment duration is 45-60 min per treatment site, with most patients receiving treatment at multiple sites. The mechanism by which the treatment promotes adipocyte cell death induced and by increasement of collagen deposition by the body cool is still not clearly understood (Pennycook, et al., 2020). However, preclinical studies suggest that a selective apoptotic process is initiated when fat cells are cooled to temperatures between −2 and 7° C. Cryolipolysis does not provoke the inflammatory response at the time of treatment. Instead, an inflammatory response begins within 3 days after treatment and the response peaks within 14 days. From day 14 to day 30, macrophages and phagocytes engulf dead lipid cells. The inflammation declines, and the lipids are safely metabolized within 90 days. According to CoolSculpting® protocol, patients typically experience at least 3 months before they see final results.

Although anesthesia is not used during cryolipolysis treatment, possible complications are reported—but no complications appear to induce long-term damage, except by paradoxical adipose hyperplasia with an incidence of 0.021% to 1.00% as per Nikolis, et al. Treatment may also cause darker skin color, hardness, discrete nodules, frostbite (local injury due to cold), hernia or worsening of existing hernia, and mild to moderate short-term dysesthesia in peripheral nerves.

RF (Radiofrequency energy) can be delivered through various tissue types (i.e., skin, fat, and muscle) to generate thermal energy—as reported by Dayan et al. Adipose tissue has a high tissue impedance and serves to generate more heat than muscle, which has a lower impedance. In fact, when RF energy is directed to subdermal adipose tissue, adipose tissue exhibits significantly higher temperatures than those of the dermis, leading to fat necrosis with epidermal preservation.

There is no standard protocol for RF treatment sessions and the range of therapeutic sessions vary between 1 and 24 weeks. Thigh circumference measurement decreased 2.45 cm on average after six treatment sessions spaced one week apart. However, there were no significant changes in body weight and blood lipids after treatment. Treatments take approximately thirty minutes and are repeated once a week for four weeks, or as determined during the assessment. The procedure is done without anesthesia.

Mild erythema has been reported. However, higher temperatures over a short time could be lethal for adipose tissue—but it is not necessarily uncomfortable for patients. Longer time (for example 8-10 minutes) with lower temperature, leads to intended adipose cells damage. Former researchers insisted that other parameters than time are related to RF success, such as: power; and frequency of treatment sessions; yet exact protocols in this field are unavailable.

Why Positive Results of CMIP are Evident Only after Several Treatment Sessions—or not at all Human skin has a semi-permeable quality, acting as a protective barrier against penetration of potentially harmful external substances. Most of this semi permeability is due to the presence of a barrier layer known as stratum corneum (SC). One problem associated with the SC is that it prevents the delivery of cosmetic substances through the skin, limiting the effectiveness of regular cosmetic treatments, as noted by Gelker et al.

CMIP Profitability Versus Expensive Equipment and Consumables

Today cosmetic professionals and many physicians offer their customers a high-value treatment with excellent quality and a typical affordable price of about $2,000 to $4,000 per treatment. In parallel, cosmetic professionals expect a return on their investment in equipment and consumables of only a few months. The latest generation of less-invasive technology devices and consumables are relatively expensive. For example, equipment purchase prices range between $10,000-$150,000. An additional consideration to the equipment purchase and consumables associated with these procedures (e.g., CoolSculpting® machine) is the annual warranty/service cost of equipment. As a result, cosmetic professionals' investment in equipment may be much less profitable than expected.

Cold Atmospheric Plasma and the Delivery of Cosmetic Substances

Cold atmospheric plasma (CAP) has been developed in the last decade as a dermo-cosmetic technology. CAP, when controllably applied on the skin surface (also referred to as "irradiation") aids in the healing of wounds, skin rejuvenation, and in treating wrinkles, as described by Graves et al. Furthermore, it is known that CAP irradiation helps as a cosmetic pretreatment to enhance the delivery of topically applied substances into the skin and the systemic circulation—as described in:

Wen X., Y. Xin, y M. R. Hamblin. 2021. «Applications of cold atmospheric plasma for transdermal drug delivery: a review» Drug Deliv. and Transl. Res. 741-747; and in Busco, G., Robert E., Chettouh-Hammas N., Pouvesle J. M., y Grillon C. 2020. «The emerging potential of cold atmospheric plasma in skin biology» Free Radic Biol Med. 290-304.

Regarding patent publications, in WIPO publication no. WO2019121968, whose disclosure is incorporated by reference, Barbarat et al. describe a non-therapeutic cosmetic process for treating human keratin materials (K), comprising the step consisting in exposing said materials (K) to a polarized cold atmospheric plasma and comprising also a topical application of a cosmetic composition before and/or during and/or after the exposure to the polarized cold atmospheric plasma.

Kalghatgi et al., in US Patent Publication no. 20150094647, whose disclosure is incorporated by reference, describe exemplary methods of opening pores and moving molecules into tissue comprising, applying plasma to the surface of tissue and applying a carrier including one or more molecules to the surface of the tissue.

In US Patent Publication no. 20140188071, whose disclosure is incorporated by reference, Jacofsky et al. describe a method and device to apply a cold plasma to a substance at a treatment surface of a patient to cause electroporation of the substance into cells of the patient; the substance can be previously applied to the treatment surface. Alternatively, the substance can be placed in a foam-like material within a tip that passes the cold plasma from the cold plasma device to the treatment area. The tip can be a cannula device with an aperture at the distal end. The cannula device can also have apertures along a portion of the length of the cannula device.

Kalghatgi et al., in US Patent Publication no. 20170246440, whose disclosure is incorporated by reference, describe apparatuses and methods for delivering bioactive substances or cosmetic substances using plasmaporation and microneedles are provided. The delivery of the substances includes topical, intracellular, intercellular, and transdermal delivery to the subject.

In WIPO publication no. WO2004056334, whose disclosure is incorporated by reference, Fleischmann describes an invention related to a mixture containing the Dead Sea salt, bicarbonate and silica and to the use of said mixture.

CAP irradiation produces small pores in the skin, without the presence of damage and enhancing percutaneous absorption of topic substances, as per Shimizu, K., K. Hayashida, y M. Blajan. 2015. «Novel method to improve transdermal drug delivery by atmospheric microplasma irradiation» Biointerphases.

Dermocosmetic Treatments

There are several dermocosmetic treatments know in the art, having anti-obesity effects, as described hereinbelow. Chemical plant products are referred to hereinbelow as phytomolecules, and they are found widely in plant extracts and essential oils. Currently, more than 80% of the world's population use plant extracts and essential oils, as indicated by McKay D L et al., 2006. Essential oils offer various benefits widely incorporated in cosmetic products because they are considered safe and nontoxic, as described by Sarkic et al., 2018. Experimental evidence suggests that the phytomolecules may exert anti-obesity effects by inhibiting adipogenesis and attenuating adipose tissue growth by inducing apoptosis and by promoting lipolysis of mature adipocytes (Sharma et al., 2018). It is noted that in most of the scientific publications about phytomolecules that influence adipose tissues, little is reported/known about the effect on cellular and molecular mechanisms, refer to Stefanon et al. Moreover, adipose tissue has been revealed as a heterogenous and complex tissue compounded by many subtypes of adipocytes and their respective contribution to tissue function remains to a large extent unclear, as per Yang Loureiro et al.

There is some experimental evidence that phytomolecules in a dermocosmetic treatment influences adipose tissues. As noted above, little is known about the effect on cellular and molecular mechanisms intervening in the process—although some clues can be found in the literature, which reflects that some phytomolecules can regulate microRNAs and downstream adipogenesis related target genes, refer to Dhar et al. During adipogenesis, microRNAs can accelerate or inhibit adipocyte differentiation and therefore they modulate cell fate, as described in Romao et al., 2011. The following is an overview of phytomolecules and minerals that can affect white adipose tissues and which are known in the art of dermocosmetic treatments.

Peppermint oil (*Mentha piperita* L.) Leaves of this plant contain many phytomolecules such as menthol and some vital elements (Ca, Na, K, Mg, Fe, Zn, Cd, Cr and Mn)—as described by Alexa et al., 2018. Recent studies suggest that in humans, menthol induces "browning" of white adipose tissues, controlling metabolism and body energy balance in a thermogenic-like activity.

Grapefruit oil (*Citrus grandis*) The main components of grapefruit have flavonoids that can be used in obesity treatment. Biological studies indicate a reduction in adipose tissue and stimulus to β-oxidation. Biological studies indicate increased expression of PPARα and its target genes. In-vitro studies indicate a reduction in adipocyte differentiation. In vitro studies indicate adipocyte lipogenesis and apoptosis, as described by Nakajima et al., 2014.

Rosemary oil (*Rosmarinus officinalis*): An herb native to the Mediterranean region and reported as having antioxidant, hepatoprotective, anti-inflammatory, and antimicrobial activities. Rosemary is a natural phenol carboxylic acid has phenolic diterpene (carnosic acid, carnosol, rosmadial, rosmanol), flavonoids phenolic acids, and essential oils. Molecular experimental results indicate that rosemary has an influence on the fat metabolism. Rosemary extract modulates human adipocyte differentiation and significantly interferes with adipogenesis and lipid metabolism, as described by Stefanon et al., 2015 and Rui et al., 2017.

Chemicals agonist of TRP receptors: Cold receptor TRP (Transient Receptor Potential) are channels triggered by different chemical agonists. An activated TRP enhances extracellular calcium influx through channels, leading to increases in intracellular Ca2+ levels. Several studies show that cold receptors TRP channels are expressed in adipocytes and are involved in energy metabolism and adipocyte heat production/thermogenesis. Refer to: Khare et al., 2019; Uchida et al., 2017; Gao et al., 2019; and Zhai et al., 2020.

Menthol: is an agonist of TRPM8 receptor, refer to McKemy et al., 2002. In a human adipocyte cell line, menthol-induced TRPM8 activation increased UCP1 gene expression, mitochondrial activation, and thermogenesis.

Nutmeg (*Myristica fragrans* Houtt): A most potent activator of a cooling channel TRPM8 found in nature is extracted from nutmeg. A nutmeg compound took five minutes to reach menthol's initial level of cooling, but the nutmeg compound cooling effect lasted longer—for 30 minutes compared with 10 minutes for menthol.

Camphor oil (*Cinnamomum camphora*): Camphor oil is extracted from the wood of camphor trees and the oil is easily absorbed through the skin. This compound has many applications in traditional medicine as an antispasmodic, antipruritic, anti-inflammatory, anti-infective, rubefacient, contraceptive, mild expectorant, nasal decongestant, and a cough suppressant. In modern medicine, it is suggested that camphor has an antioxidant effect, insulin, and a wound healing potency. Camphor can reduce body weight and fat deposition by activating the TRPV3 channel. In the same way as the camphor, black pepper can activate the TRPV3 channel.

Dead sea salt and minerals (DS) are known for their cosmetic properties due to the special salt composition of found in Dead Sea water, as reported by Bawab, et al. Chemical analysis of Dead Sea mud samples reveals high concentrations of salts (CaO, CO2, SiO2, chlorides, and sulfates) and other minerals (Barium, Vanadium, Strontium, lead, cadmium, and zinc) as described by Khlaifat et al. The moisturizing and smoothing effect of DS water on skin makes it widely used in dermo-cosmetic products. It was shown that high magnesium content enhances water retention in the skin. Additionally, used as a bath additive, a mixture containing Dead Sea salt, bicarbonate, and silica leads to treatment of slags, the removal of residual metabolism products, and the excitation of metabolism, and, as a consequence, to the reduction in weight, as described by Fleischmann in WIPO publication no. WO2004056334, hereinabove. Apparently, these effects are explained by the relatively high osmotic pressure found in bath water containing DS additives.

There is therefore a need for a CMIP directed to reducing body size, the treatment yielding repeatable and near-immediate results, and taking advantage of a dermocosmetic formula integrated with CAP, directed to avoiding physical damage to the skin while using relatively inexpensive and proven equipment.

SUMMARY OF INVENTION

According to the teachings of the current invention, there is provided a cosmetic treatment for reducing body size, incorporating a cosmetic minimally-invasive procedure (CMIP) and incorporating cold atmospheric plasma irradiation (CAP) of a body, the treatment comprising the five steps of: a first step of preparing a cosmetic composition and applying the composition to the body to form a mask on the body; a second step of using a gypsum plaster of Paris (POP) and sealing the mask; a third step of wrapping the POP with a nylon/plastic wrap; a fourth step of preparing the body with a layer of aqueous surface gel; and a fifth step of using CAP irradiation of the body; whereby the body is an abdominal region, and the body size is indicated by at least three representative body circumference measurements; and whereby body size reduction is statistically significant when comparing before and after cosmetic treatment body sizes. Preferably, the abdominal region is located approximately from beneath the breasts to above the waist and around the back. Most preferably, preparing the cosmetic composition further comprises gently mixing green clay, dead sea salt, pure essential oils, and organic and inorganic compounds with approximately 40 ml of warm water to create a mud. Typically, the cosmetic composition includes: 42% green clay; 58% DS salt and minerals; 10 drops, respectively, of essential oils: peppermint oil, grapefruit oil, and rosemary oil; and 10 to 20 drops of camphor oil, with percentages indicating percentage by mass. Most typically, the cosmetic composition is adapted to increase thermogenic behavior of fat tissues, the composition having an addition of approximately 1 to 5 grams menthol powder; 0.5 to 1 grams of black pepper powder; and 10-20 drops of nutmeg.

Preferably, the second step is applied immediately following the first step to seal the mask and to enhance impregnation of the mask on the body. Most preferably, the third step is performed immediately following completion of second step, the nylon/plastic wrap serving to maintain humidity of the POP and of the mask, further serving to thoroughly impregnate the skin of the body with ingredients of the cosmetic composition. Typically, the third step further includes maintaining the nylon/plastic wrap in position for a time period of at least 40 minutes. Most typically, the time period is up to 120 minutes.

Preferably, the third step further includes using a low-level laser therapy (LLLT) belt having 325 LEDs (red 660 nm and infrared 850 nm), the LLLT belt activated for the entire time period and removed when the time period ends. Most preferably, at the end of the time period, the nylon/plastic wrap, the POP, and the mask are removed and are cleaned from the body. Typically, the fifth step is performed substantially immediately upon completion of the fourth step, the fifth step including using a CAP electrode of a cold plasma device for application of CAP irradiation to uniformly apply a dose equivalent to 6 to 8 minutes at maximum power per 100 cm$^2$ body area. Most typically, body sizes are measured as respective before and after measurements, wherein the respective before measurements are made within one hour before the first step and the respective after measurements are made within 10 minutes after the completion of the fifth step. Preferably, respective before and after body size measurements are compared to yield respective body size differences, indicative of body size reduction. Most preferably, respective body size differences and respective body size reduction are statistically significant.

LIST OF FIGURES

The invention is described herein, by way of example only, with reference to the accompanying drawings, wherein.

Figure 5:
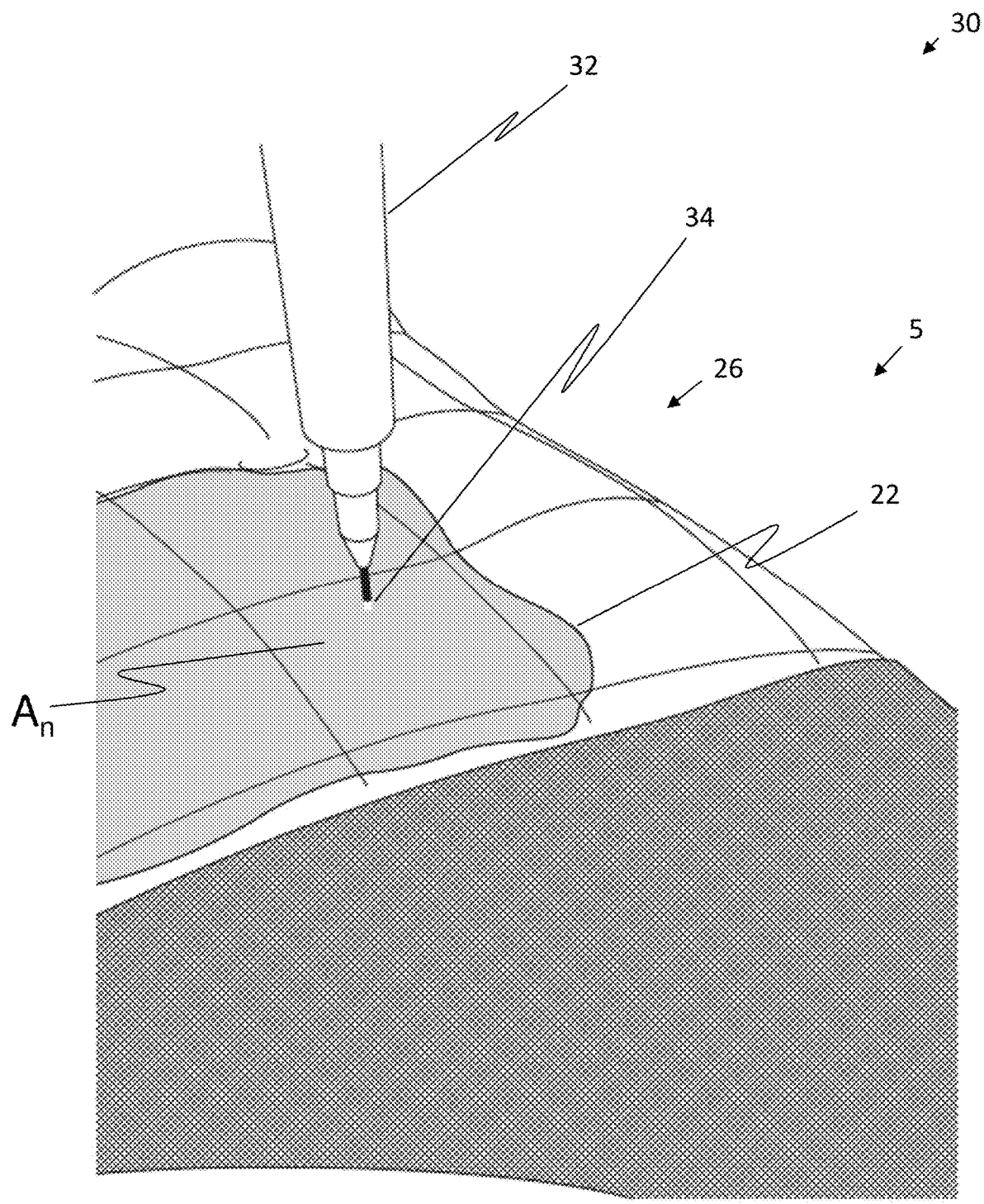
Figure 6:
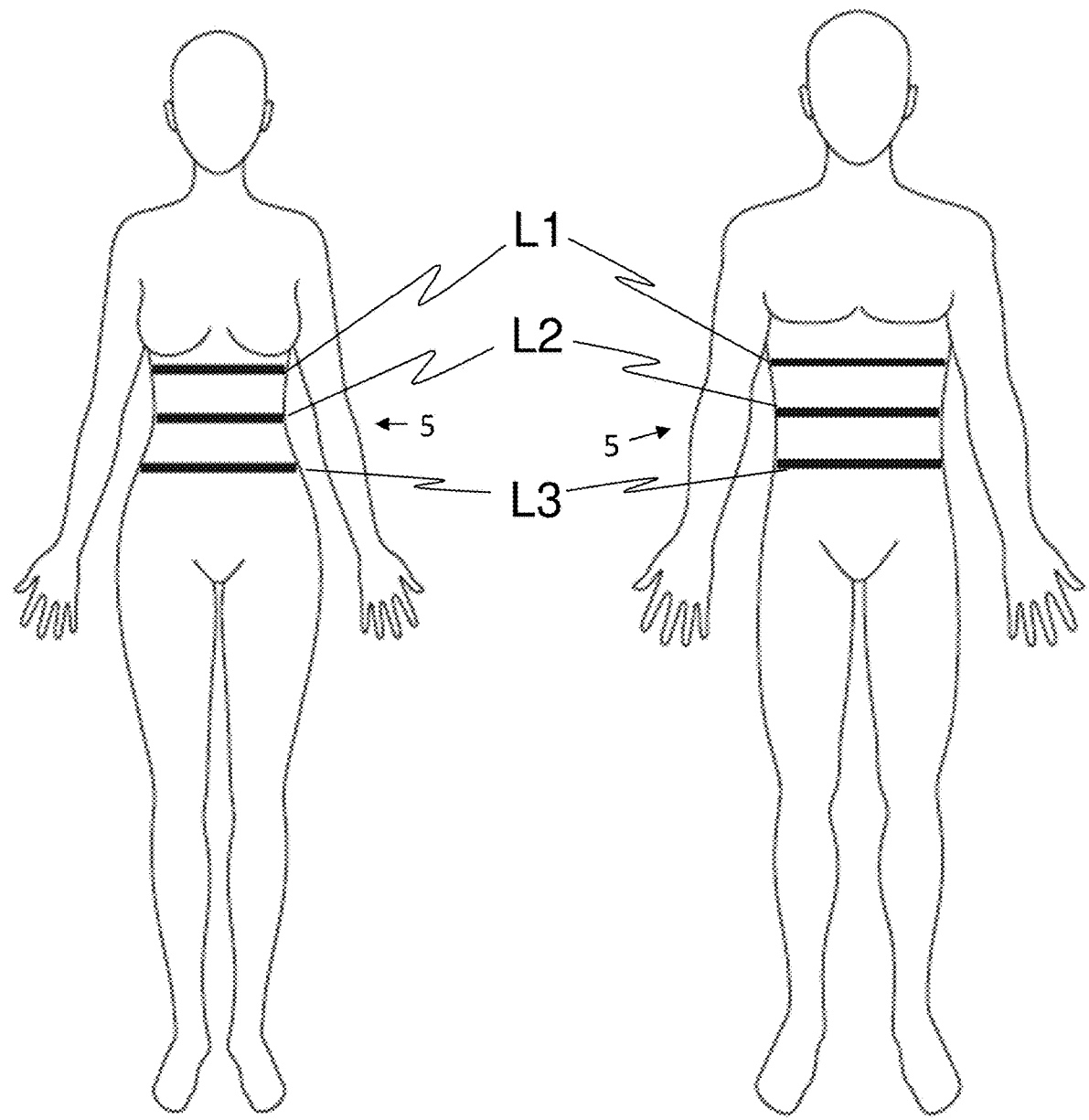
Figure 7A:
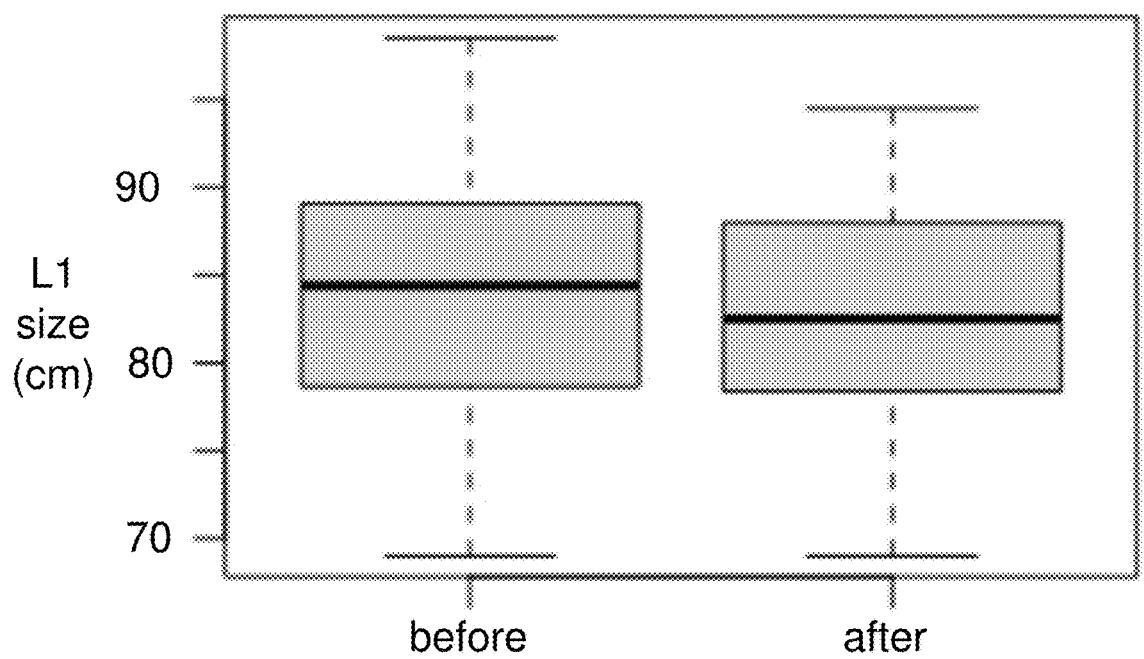
Figure 7B:
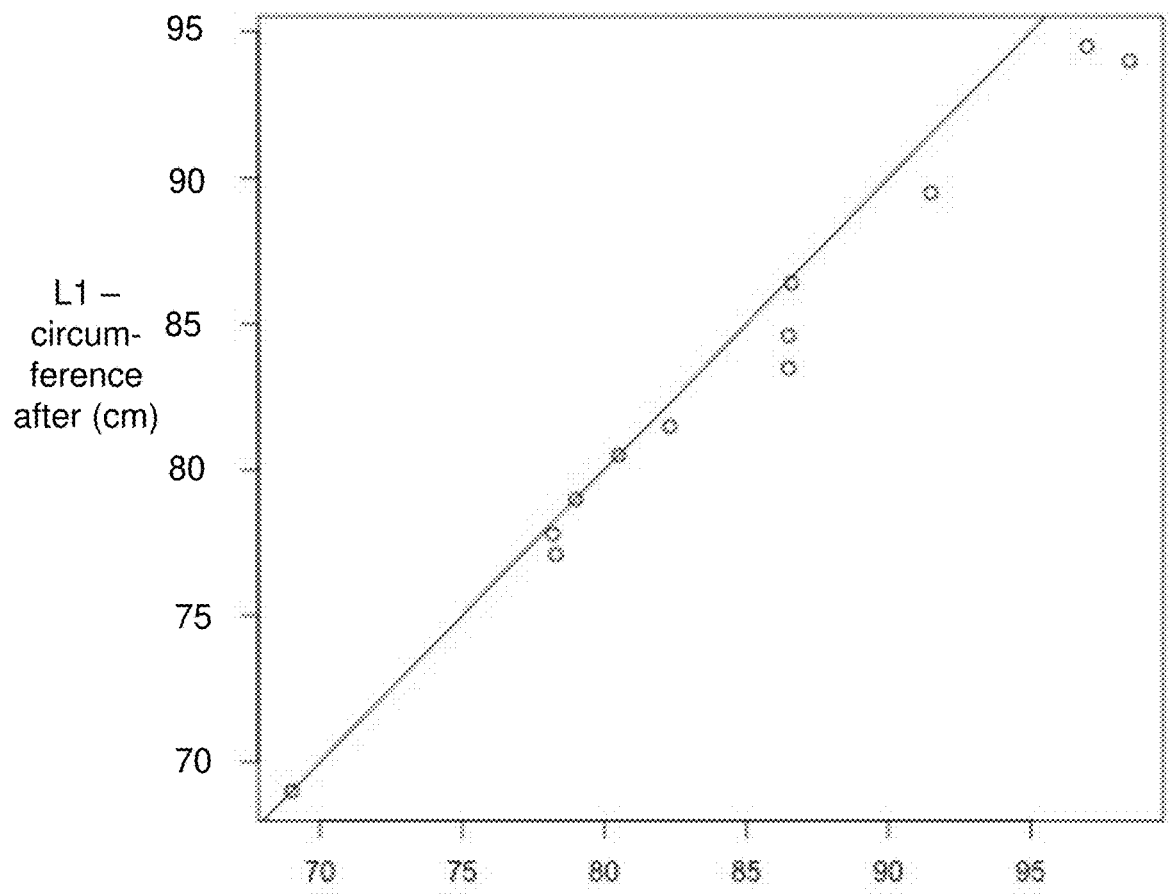
Figure 8A:
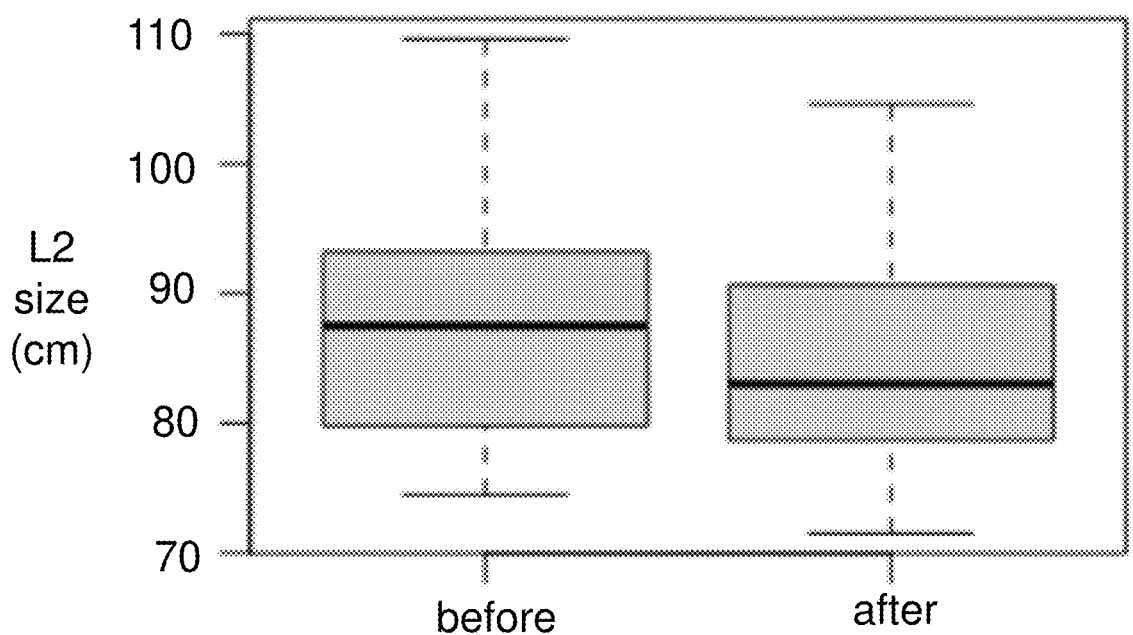
Figure 8B:
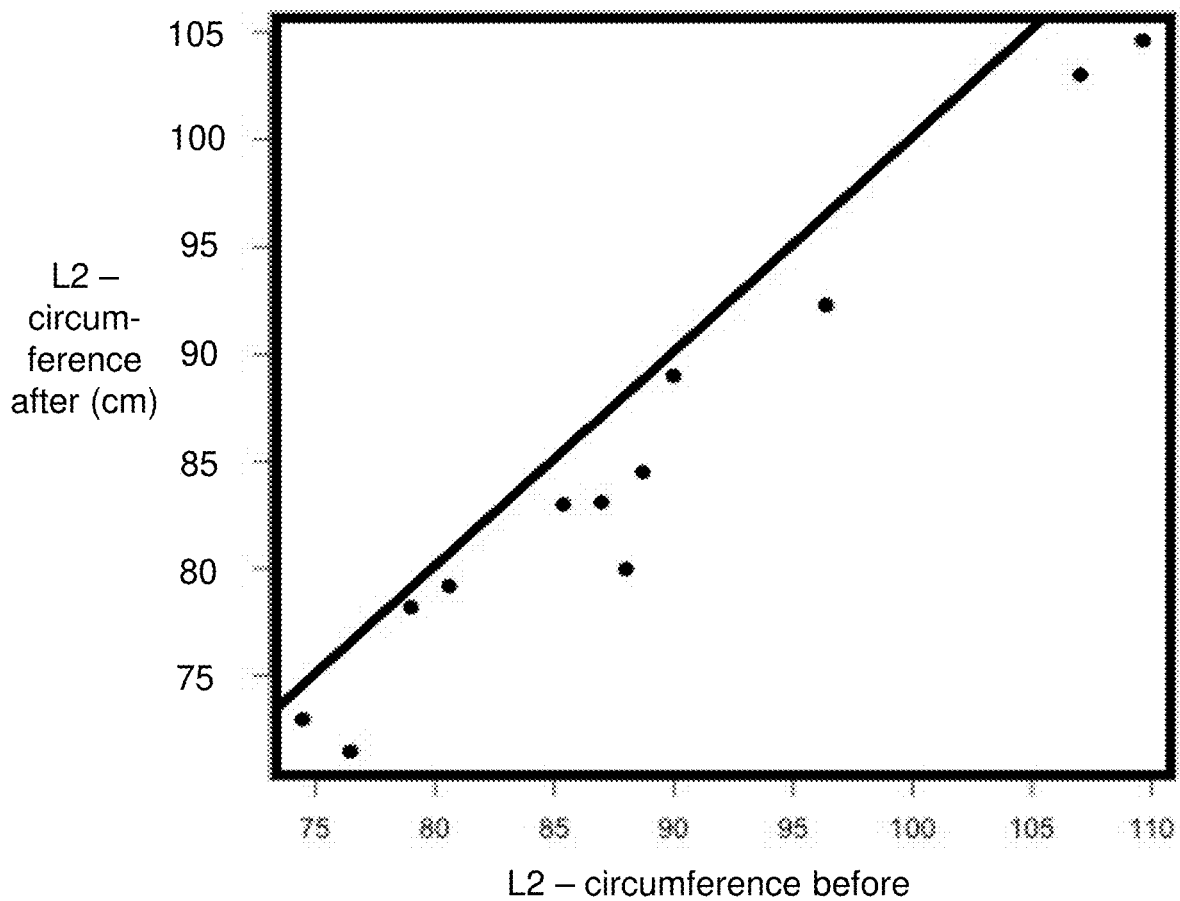
Figure 9A:
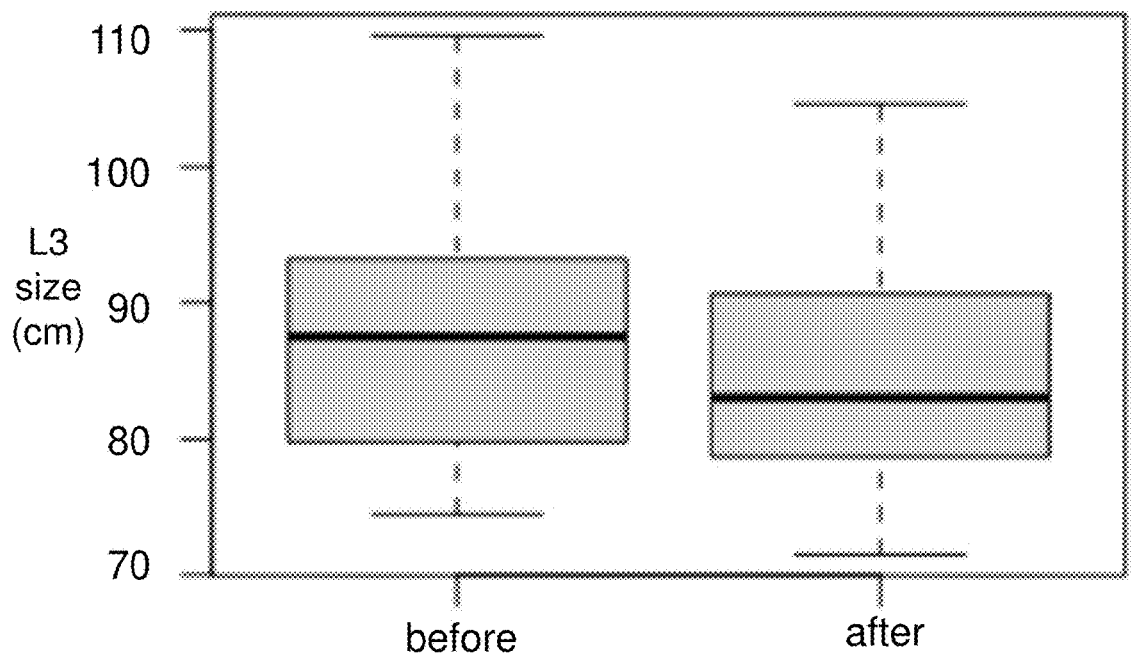
Figure 9B:
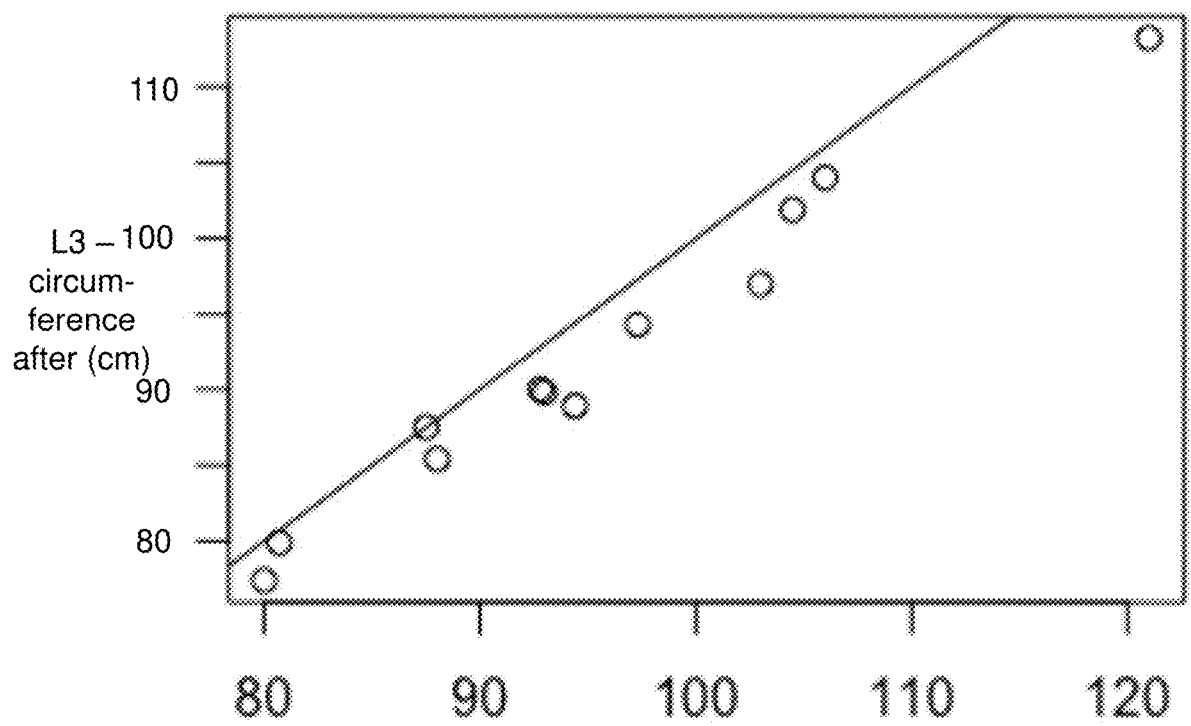

FIG. 5 is a pictorial representation of a fifth step of the cosmetic treatment for reducing body size, the fifth step including a CAP irradiation of the body, in accordance with an embodiment of the current invention FIG. 6 is a pictorial representation of the body of a female and a male figure, showing three body sizes: L1, L2, and L3, in accordance with embodiments of the current invention; and FIGS. 7A, 8A, and 9A are respective box-data-plots of "before" and "after" body sizes L1, L2, and L3, and FIGS. 7B, 8B, and 9B are, respective standard data plots of "after" body sizes L1, L2, and L3, in accordance with embodiments of the current invention.

DETAILED DESCRIPTION

Embodiments of the current invention relate to the field of cosmetic treatments and specifically to a cosmetic treatment reducing body size.

Embodiments of the current invention are directed to provide a novel and non-invasive cosmetic treatment using electroporation properties of cold atmospheric plasma (CAP) to obtain near-immediate results and reduce body size by as much as 8 cm. Embodiments of the current invention include a novel formula mask which serves to produce a cooling sensation, triggering a thermogenic process, and inducing "browning" in adipocytes—as further described hereinbelow.

Embodiments of the current invention include combining a non-invasive topical application of the phytomolecules and DS, in concert with electroporation properties of CAP to enable and enhance effectiveness of a topical application treatment without causing physical damage to the skin. This combination of the advantages of two biophysical processes—namely electroporation of molecules and adipocyte thermogenesis—has been found to have a novel and unexpected effect on body size (alternatively referred to as "body contouring") expressed in a significant reduction of at least 3 representative body circumference measurements.

The non-invasive topical application of phytomolecules and DS (interchangeably referred to hereinbelow as: a "cosmetic composition"; a "mask"; and a "mud mask") has a cooling effect on the human body, which serves to mimic cold exposure. Sun et al, review the role of the TRP channels on adipocyte thermogenesis. Temperatures below 28° C. can serve to activate these channels to the defense thermoregulatory system, increasing the thermogenesis in white tissues. The cold receptors (TRPM8 and TRPV3) activated in the human white adipocytes induce a brown-like phenotype or "browning" effect. TRPM8 can be activated by chemicals agonists such as menthol and nutmeg (ACS Med Chem Lett. 2017 May 31; 8(7):715-719), and TRPV3 can be activated by camphor (Pharmaceuticals (Basel). 2016 Sep. 9; 9(3). Moreover, other TRP's can be activated by various stimuli different from cool but producing the same effect. E.g., TRPV1 can be stimulated by black pepper and other foods that up-regulate the expression of thermogenic genes and induce "browning" in adipocytes Okumura et al.

Figure 1:
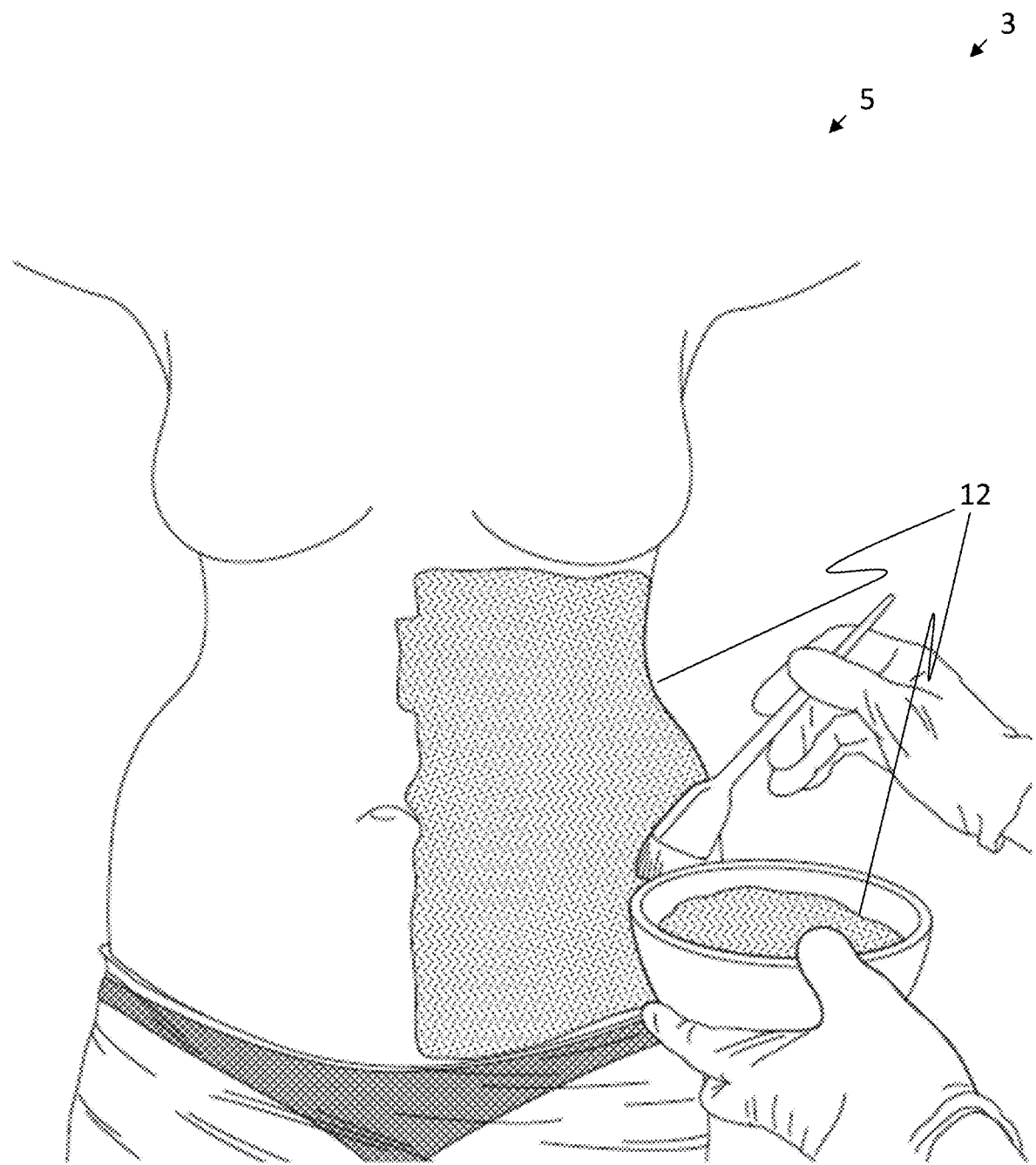
FIG. 1 is a pictorial representation of a first step of a cosmetic treatment for reducing body size, including a body and an application of a cosmetic composition upon the body, in accordance with embodiments of the current invention.

Reference is currently made to FIG. 1, which is a pictorial representation of a first step 3 of a cosmetic treatment for reducing body size, including a body 5 and an application of a cosmetic composition 12 upon body 5, in accordance with embodiments of the current invention. In the specification and claims which follow hereinbelow, the term "body" is intended to mean the abdominal region—that is, a region approximately from beneath the breasts to above the waist, including around the back. Additionally, it is noted that the steps of the cosmetic treatment are all performed on/at the skin of the body—and the term "body", as used in conjunction with the steps of the cosmetic treatment described hereinbelow and in the claims, is additionally intended to mean the "skin of the body".

Cosmetic composition 12, once applied to the body, is referred to hereinbelow as a "mask" and/or a "mud mask". The mud mask includes a balance of Dead Sea (DS) minerals and is enriched with essential oils and chemical phytomolecules. Before the first step of the cosmetic treatment, a cleaning and mechanical peeling of the skin is performed using a mixture of white sugar (5 gr. or 50%) and liquid hypoallergenic soap (5 gr. or 50%).

As shown in FIG. 1, the cosmetic composition is applied on the body following cleaning, as known in the art. Green clay, dead sea salt, pure essential oils, and organic and inorganic compounds are gently mixed with approximately 40 ml of warm water to create a mud. Cosmetic composition 12 includes: 74 grams green clay (42%); 106 grams DS salt and minerals (58%); 10 drops, respectively, of essential oils: Peppermint oil (*Mentha piperita* L.), Grapefruit Oil (*Citrus grandis*), and Rosemary oil (*Rosmarinus officinalis*); and 10 to 20 drops of Camphor oil (*Cinnamomum camphora*). All percentages mentioned herein are percentages by mass, unless otherwise indicated.

The cosmetic composition may be adapted to increase thermogenic behavior of fat tissues, the composition having an addition of approximately: 1-5 grams menthol powder; 0.5 to 1 grams of black pepper powder; and 10-20 drops of nutmeg (*Myristica fragrans* Houtt).

Figure 2:
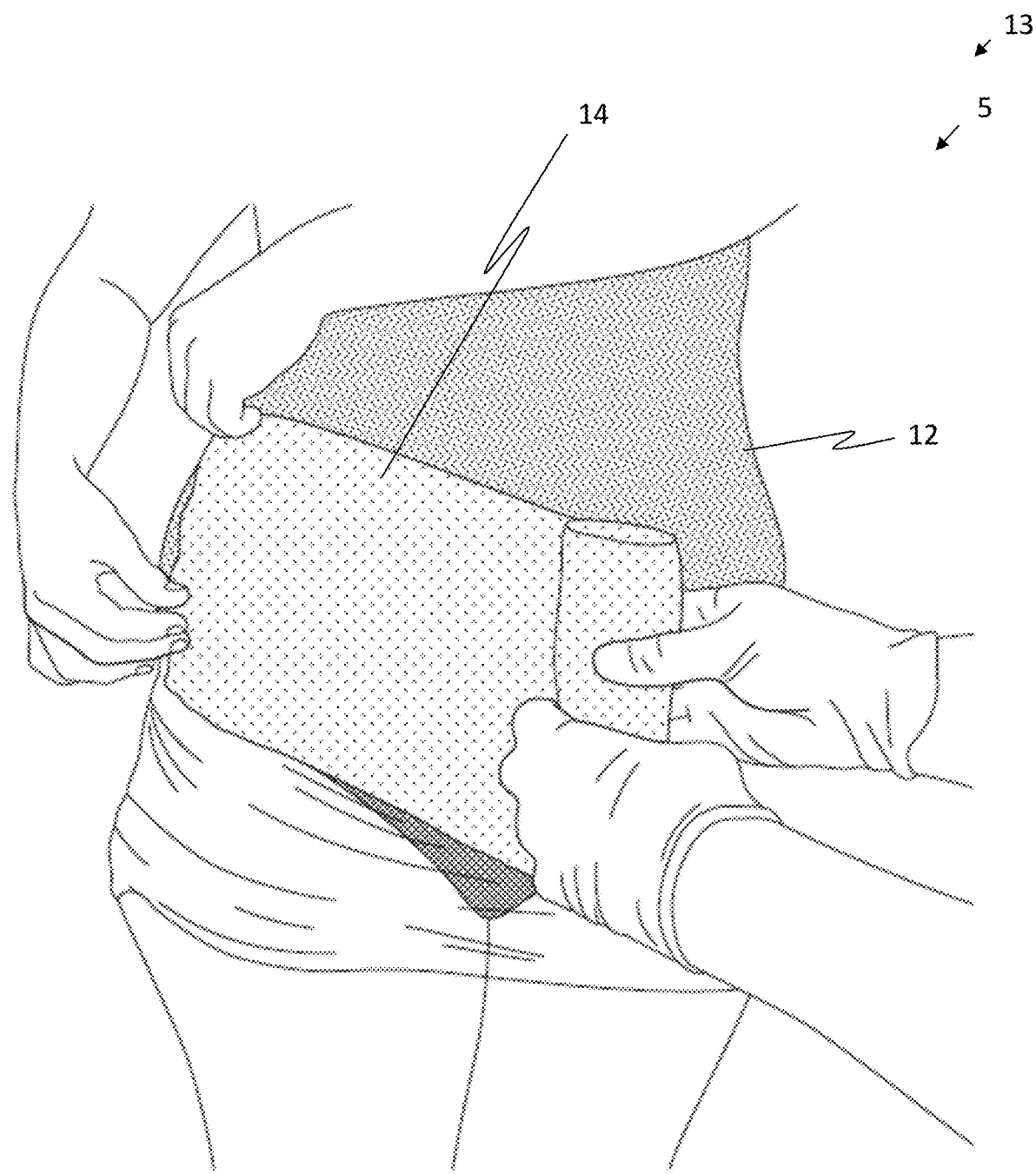
FIG. 2 is a pictorial representation of a second step of the cosmetic treatment for reducing body size, the second step including sealing mask 12 of FIG. 1, using a gypsum plaster of Paris bandage (POP), in accordance with embodiments of the current invention.

Reference is currently made to FIG. 2, which is a pictorial representation of a second step 13 of the cosmetic treatment for reducing body size, the second step including sealing mask 12 of FIG. 1, using a gypsum plaster of Paris bandage (POP) 14, in accordance with embodiments of the current invention. Apart from differences described below, body 5 and mask 12 of FIG. 2 are identical in notation, configuration, and functionality as described in FIG. 1 hereinabove.

POP 14 of second step 13 is applied immediately following first step 3 of FIG. 1 to seal the mask and to enhance impregnation of the mask on the body. The POP is first submerged in warm water, as known in the art, and then applied on the body covered by the mask.

Figure 3:
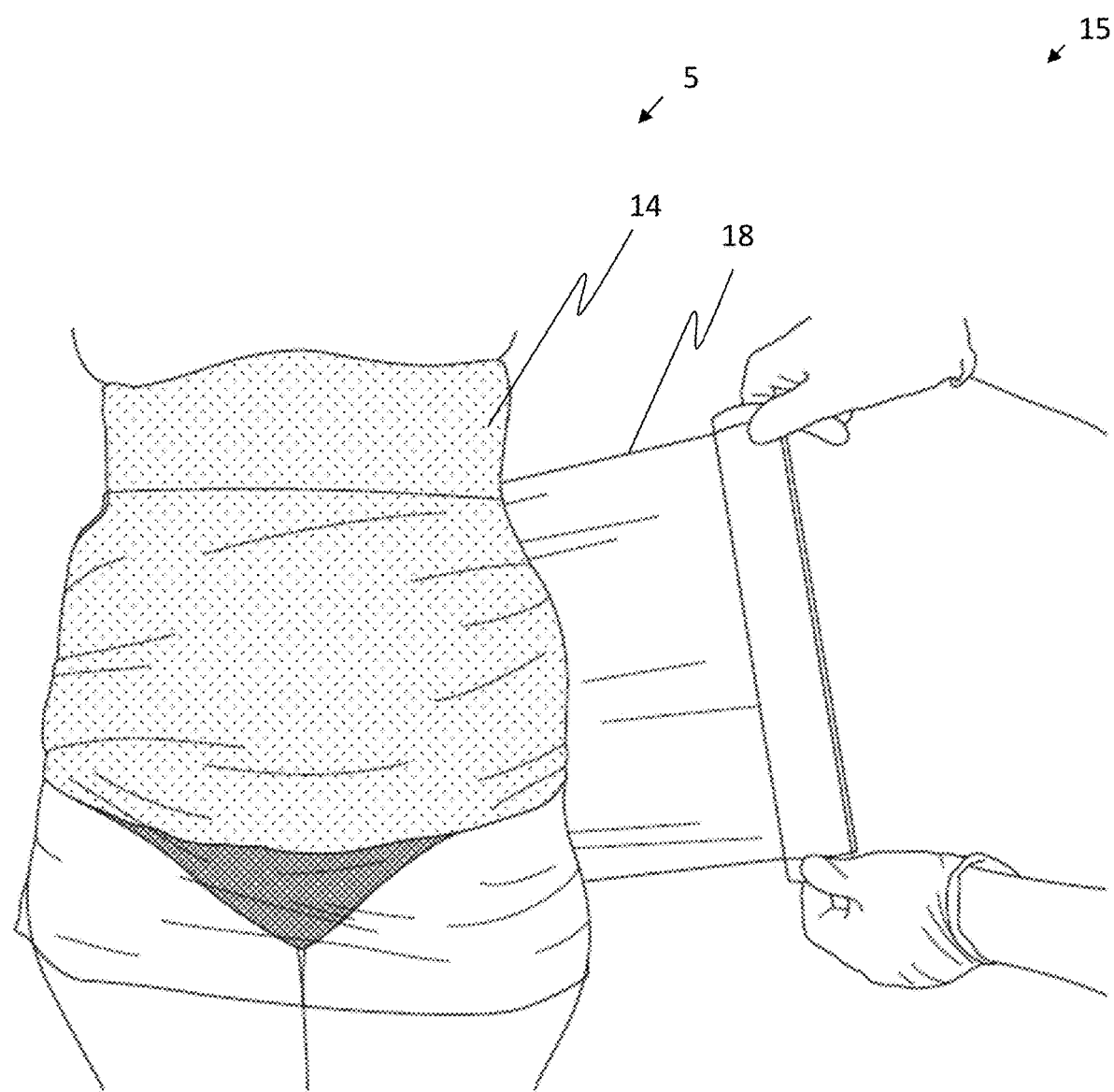
FIG. 3 is a pictorial representation of a third step of the cosmetic treatment for reducing body size, the third step including wrapping the POP with a nylon/plastic wrap, in accordance with an embodiment of the current invention.

Reference is currently made to FIG. 3, which is a pictorial representation of a third step 15 of the cosmetic treatment for reducing body size, the third step including wrapping the POP with a nylon/plastic wrap 18, in accordance with an embodiment of the current invention. Apart from differences described below, body 5, mask 12, and POP 14 of FIG. 3 are identical in notation, configuration, and functionality as described in FIG. 2 hereinabove. Third step 15 is performed immediately following completion of second step 13. Nylon/plastic wrap 18 serves to maintain humidity of the POP and of the mask, further serving to thoroughly impregnate the skin of the body with ingredients of the cosmetic composition.

Third step 15 further includes maintaining the nylon/plastic wrap in position for a time period of at least 40 and preferably as much as 120 minutes to enhance impregnation, as noted hereinabove. Whereas the POP serves to emit heat as it sets, the cosmetic composition serves to impart a cooling effect, as noted hereinabove.

Optionally, the third step can include using a low-level laser therapy (LLLT) belt having 325 LEDs (red 660 nm and infrared 850 nm)—not shown in the current figure. The LLLT belt is activated for the entire time period and is removed when the time period ends.

At the end of the time period the nylon/plastic wrap, the POP, and the mask are removed and are cleaned from the body.

Figure 4:
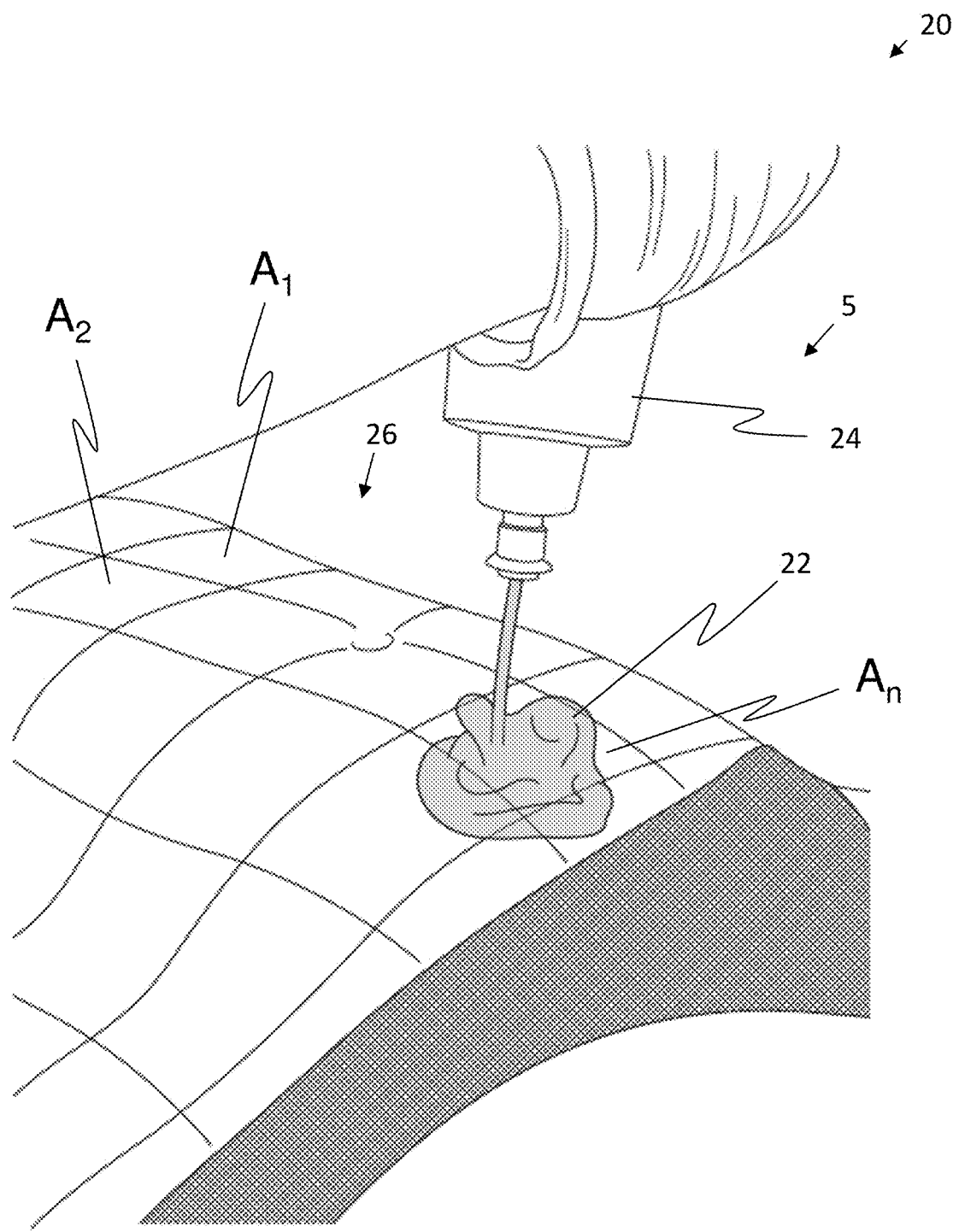
FIG. 4 is a pictorial representation of a fourth step of the cosmetic treatment for reducing body size, the fourth step including preparation of the body with a layer of aqueous surface gel, in accordance with an embodiment of the current invention.

Reference is currently made to FIG. 4, which is a pictorial representation of a fourth step 20 of the cosmetic treatment for reducing body size, the fourth step including preparation of the body with a layer of aqueous surface gel 22, in accordance with an embodiment of the current invention. Apart from differences described below, body 5 of FIG. 4 is identical in notation, configuration, and functionality as described in FIGS. 1-3 hereinabove. Prior to the fourth step 20, mud 12 (ref FIGS. 1-2) is removed/cleaned with a moistened fabric or shower. After cleaning, a layer of aqueous surface gel 22 is applied to the entire body with an exemplary squirt bottle 24. (For purposes of clarity, aqueous surface gel 22 is represented in the current and subsequent figures as partially covering the body—however, it is to be understood that the aqueous surface gel is applied uniformly to the entire body.)

Application of the aqueous surface gel is in preparation of a subsequent step including CAP irradiation. Aqueous surface gel 22 serves to protect the skin and to avoid/prevent burning during CAP irradiation. Additionally, the aqueous surface gel allows CAP-generated ionized gases to penetrate to the skin and to stimulate the collagen synthesis in the conjunctive tissue.

Following cleaning, as described above, fourth step 20 optionally includes drawing a grid 26 on the body, the grid defining approximate rectangular-shaped quadrants having respective areas $A_1, A_2, \ldots A_n$, as indicated in the figure. The respective areas, effectively defining a total body area, serve to aid in administering a correct dose of CAP irradiation, as described further hereinbelow.

Reference is currently made to FIG. 5, which is a pictorial representation of a fifth step 30 of the cosmetic treatment for reducing body size, the fifth step including a CAP irradiation of the body, in accordance with an embodiment of the current invention. Apart from differences described below, body 5, aqueous surface gel 22, and grid 26 of FIG. 5 are identical in notation, configuration, and functionality as described in FIG. 4 hereinabove. The fifth step is performed substantially immediately upon completion of the fourth step.

The CAP irradiation is applied using a CAP electrode 32, having an exemplary CAP jet 34. The CAP irradiation is applied uniformly over respective areas in a dose equivalent to 6 to 8 minutes at maximum power per 100 cm$^2$ of body area. The grid, described hereinabove, serves to assist in correctly applying the CAP irradiation over the body area. The CAP irradiation serves to open small pores, allowing the composition to be delivered into the skin, as noted previously hereinabove. Completion of the cosmetic treatment and of the fifth step includes cleaning the body, as known in the art.

Specifications of an appropriate cold plasma device for application of CAP irradiation include:
  operation at temperatures from +10° C. to +35° C. and
    ambient relative humidity up to 80% and up to 25° C.
  High-frequency oscillation frequency, kHz—440+/−2.5%
  Load range, Ohm—from 100 to 2000
  Rated load, Ohm—300
  Maximum output power at 1 output, W (monopolar contact coagulation)—15

An exemplary cold plasma device, having similar specifications as above and used in actual treatments with body size data presented hereinbelow, is "Me-si", Aviamotornaya St 6, building 7, 11111-6 Moscow, Russia.

Reference is currently made to FIG. 6, which is a pictorial representation of body 5 of a female and a male figure, showing three body sizes: L1, L2, and L3, in accordance with embodiments of the current invention. Apart from differences described below, body 5 is identical in notation, configuration, and functionality as described in the previous figures hereinabove. Body sizes L1, L2, and L3 represent three representative body circumference measurements, measured approximately 10 cm apart, from beneath the breasts to approximately at the waist, as shown in the figure. Body sizes L1, L2, and L3 are used to perform "before" and "after" measurements of a representative sample of more than 10 individuals who received the cosmetic treatment for reducing body size described hereinabove. "Before" measurements are made within one hour before the start of cosmetic treatment; and "after" measurements are made within 10 minutes following the completion of the cosmetic treatment. Measured data of body sizes L1, L2, and L3 are presented in the series of figures which follow hereinbelow.

Reference is currently made to FIGS. 7A, 8A, and 9A, which are respective box-data-plots of "before" and "after" body sizes L1, L2, and L3, and of FIGS. 7B, 8B, and 9B, and 9B, which are, respective standard data plots of "after" body sizes L1, L2, and L3, in accordance with embodiments of the current invention. In all cases, in comparing "before" and "after" body size differences (i.e., reduction in circumference) of "before" versus "after" were found to be statistically significant, as detailed below.

Referring to FIG. 7A, Box Plot indicating "before" and "after" of body size L1, with a sample size n=12, all individuals had a body size reduction with the before-after differences being statically significant between the samples (Paired t-test, t=3.3155, df=11, p-value=0.006, mean of the differences=1.375 cm).

Referring to FIG. 7B, showing differences of "before" and "after" L1 body sizes, there would be no differences when the L1 data points coincide with the 45-degree line in the plot. L1 data points beneath the 45-degree line graphically indicate a body size reduction.

Referring to FIG. 8A, Box Plot indicating "before" and "after" of body size L2, with a sample size n=12, all individuals had a body size reduction with the before-after differences being statically significant between the samples (Paired t-test t=5.6414, df=11, p-value=0.00015, mean of the differences=3.44 cm).

Referring to FIG. 8B, showing differences of "before" and "after" L2 body sizes, there would be no differences when the L2 data points coincide with the 45-degree line in the plot. L2 data points beneath the 45-degree line graphically indicate a body size reduction.

Referring to FIG. 9A, Box Plot indicating "before" and "after" of body size L3, with a sample size n=12, all individuals had a body size reduction with the before-after differences being statically significant between the samples (Paired t=5.1164, df=11, p-value=0.0003, mean of the differences=3.24 cm).

Referring to FIG. 9B, showing differences of "before" and "after" L3 body sizes, there would be no differences when the L3 data points coincide with the 45-degree line in the plot. L3 data points beneath the 45-degree line graphically indicate a body size reduction.

It is noted that the cosmetic treatment described hereinabove with regard to the "abdomen" may optionally be adapted to other regions where fat/dimension reduction is desired.

It will be appreciated that the above descriptions are intended only to serve as examples, and that many other embodiments are possible within the scope of the present invention as defined in the appended claims.

The invention claimed is:

1. A minimally-invasive cosmetic treatment for reducing body size, incorporating cold atmospheric plasma irradiation (CAP) of a body, the cosmetic treatment comprising the five steps of:
   a first step of preparing a cosmetic composition, the cosmetic composition including: 42% green clay; 58% Dead Sea salt (DS salt) and minerals; 10 drops, respectively, of essential oils: peppermint oil, grapefruit oil, and rosemary oil; and 10 to 20 drops of camphor oil, with percentages indication percentage by mass, mixed with approximately 40 ml of warm water to create a mud, and applying the cosmetic composition to the body to form a mask on the body;
   a second step of wrapping a gypsum plaster of Paris bandage (POP) around the body to seal the mask;
   a third step of wrapping the POP with a nylon/plastic wrap;
   a fourth step of removing the nylon/plastic wrap, the POP, and the cosmetic composition, and applying a layer of an aqueous gel over the body; and
   a fifth step of applying CAP irradiation to the body;
whereby the body is an abdominal region, located approximately from beneath the breasts to above the waist and around the back, and the body size is indicated by at least three representative body circumference measurements; and whereby body size reduction is statistically significant when comparing body sizes before and after the cosmetic treatment.

2. The cosmetic treatment of claim 1, whereby the cosmetic composition is adapted to increase thermogenic behavior of fat tissues, the composition having an addition of approximately 1 to 5 grams menthol powder; 0.5 to 1 grams of black pepper powder; and 10-20 drops of nutmeg.

3. The cosmetic treatment of claim 2, whereby the second step is applied immediately following the first step to seal the mask and to enhance impregnation of the mask on the body.

4. The cosmetic treatment of claim 3, whereby the third step is performed immediately following completion of second step, the nylon/plastic wrap serving to maintain humidity of the POP and of the mask, further serving to thoroughly impregnate the skin of the body with ingredients of the cosmetic composition.

5. The cosmetic treatment of claim 4, whereby the third step further includes maintaining the nylon/plastic wrap in position for a time period of at least 40 minutes.

6. The cosmetic treatment of claim 5, whereby the time period is up to 120 minutes.

7. The cosmetic treatment of claim 6, whereby the third step further includes using a low-level laser therapy (LLLT) belt having 325 LEDs (red 660 nm and infrared 850 nm), the LLLT belt activated for the entire time period and removed when the time period ends.

8. The cosmetic treatment of claim 5, whereby at the end of the time period, the nylon/plastic wrap, the POP, and the mask are removed and are cleaned from the body.

9. The cosmetic treatment of claim 8, whereby the fifth step is performed substantially immediately upon completion of the fourth step, the fifth step including using a CAP electrode of a cold plasma device for application of CAP irradiation to uniformly apply a dose equivalent to 6 to 8 minutes at maximum power per 100 $cm^2$ body area.

10. The cosmetic treatment of claim 9, whereby body sizes are measured as respective before and after measurements, wherein the respective before measurements are made within one hour before the first step and the respective after measurements are made within 10 minutes after the completion of the fifth step.

11. The cosmetic treatment of claim 10, whereby respective before and after body size measurements are compared to yield respective body size differences, indicative of body size reduction.

12. The cosmetic treatment of claim 11, whereby respective body size differences and respective body size reduction are statistically significant.

* * * * *